United States Patent
Hori et al.

(10) Patent No.: US 8,638,034 B2
(45) Date of Patent: Jan. 28, 2014

(54) MULTI-MICRO HOLLOW CATHODE LIGHT SOURCE AND ATOMIC ABSORPTION SEPCTROMETER

(75) Inventors: Masaru Hori, Nagoya (JP); Masafumi Ito, Nagoya (JP); Takayuki Ohta, Nagoya (JP); Hiroyuki Kano, Miyoshi (JP); Koji Yamakawa, Yokohama (JP)

(73) Assignees: National University Corporation Nagoya University, Nagoya-Shi, Aichi (JP); Meijo University, Nagoya-Shi, Aichi (JP); Nu Eco Engineering Co., Ltd., Miyoshi-Shi, Aichi (JP); Katagiri Engineering Co., Ltd., Yokohama-Shi, Kanagawa (JP)

( * ) Notice: Subject to any disclaimer, the term of this patent is extended or adjusted under 35 U.S.C. 154(b) by 0 days.

(21) Appl. No.: 13/578,171

(22) PCT Filed: Feb. 8, 2011

(86) PCT No.: PCT/JP2011/000685
§ 371 (c)(1),
(2), (4) Date: Oct. 4, 2012

(87) PCT Pub. No.: WO2011/102094
PCT Pub. Date: Aug. 25, 2011

(65) Prior Publication Data
US 2013/0027697 A1    Jan. 31, 2013

(30) Foreign Application Priority Data
Feb. 22, 2010 (JP) .................................. 2010-036315

(51) Int. Cl.
*H01J 17/16* (2012.01)

(52) U.S. Cl.
USPC ............................ 313/618; 313/631; 313/582

(58) Field of Classification Search
USPC .......................... 313/618, 631, 582–587, 491
See application file for complete search history.

(56) References Cited

U.S. PATENT DOCUMENTS

2007/0017636 A1    1/2007   Goto et al.
2009/0310134 A1    12/2009   Hori et al.

FOREIGN PATENT DOCUMENTS

| JP | 2005-285679 A | 10/2005 |
|---|---|---|
| JP | 2007-257900 A | 10/2007 |
| WO | 2004/107825 A1 | 2/2004 |

OTHER PUBLICATIONS

International Search Report in PCT/JP2011/000685 dated May 17, 2011 (English Translation Thereof).

*Primary Examiner* — Joseph L Williams
(74) *Attorney, Agent, or Firm* — McGinn IP Law Group, PLLC

(57) ABSTRACT

The multi-micro hollow cathode light source has a cathode plate, an insulation plate, an anode plate, and metal pieces. The insulation plate is sandwiched by the cathode plate and the anode plate. The cathode plate is made of copper. The centers of the cathode plate, insulation plate, and anode plate, are provided with holes, respectively. The holes form a penetrating though-hole. Linear slots are disposed in the cathode plate continuously extending from the hole in a cross shape. Each slot penetrates the cathode plate. Four metal pieces made of materials different from one another are inserted and buried in the four slots.

20 Claims, 3 Drawing Sheets

MULTI-MICRO HOLLOW CATHODE LIGHT SOURCE AND ATOMIC ABSORPTION SEPCTROMETER

TECHNICAL FIELD

The present invention relates to a multi-micro hollow cathode light source which can be employed in simultaneous multiple element absorption spectrometry and which allows simultaneous multiple-point light emission, and to an atomic absorption spectrometer using the light source.

BACKGROUND ART

Atomic absorption spectrometry is a well-known method for quantitating a micro-amount metal contained in a sample at high precision. In atomic absorption spectrometry, a sample is atomized at high temperature, and the atmosphere containing the atomized sample is irradiated with light. The absorption spectrum of the micro-amount metal contained in the sample is quantitated from the corresponding absorption spectrum. In atomic absorption spectrometry, a light source that emits the bright line spectrum of an analysis target element is required. When a plurality of elements are analyzed, the corresponding light sources that emit bright line spectra of the elements are required.

Patent Document 1 discloses a multi-micro hollow cathode light source as a light source that provides bright line spectra of such elements. The light source disclosed in Patent Document 1 has an anode plate, an insulation plate, and a cathode plate made of copper or copper alloy stacked together; a plurality of through-holes penetrating the stacked structure and each having a diameter of 1 cm or less; and metal plates that provide bright line spectra of interest at openings of the through-holes at the cathode plate, whereby the corresponding bright line spectra of a plurality of metal elements are provided. In other words, the light source disclosed in Patent Document 1 is a single-point light source providing a plurality of types of hollow cathode discharge corresponding to the metal elements of interest.

PRIOR ART DOCUMENTS

Patent Documents

Patent Document 1: Japanese Patent Application Laid-Open (kokai) No. 2007-257900

SUMMARY OF THE INVENTION

Problems to be Solved by the Invention

However, the multi-micro hollow cathode light source disclosed in Patent Document 1 encounters difficulty in controlling hollow cathode discharge provided from a plurality of single-point light sources. Also, for extraction of light, the multi-micro hollow cathode light source disclosed in Patent Document 1 must employ complex optical paths corresponding to the single-point light sources, requiring a cumbersome and high-cost production process, which is problematic.

Thus, an object of the present invention is to provide a light source which can provide bright line spectra attributed to a plurality of elements and which is formed of one single-point light source based on hollow cathode discharge.

Means for Solving the Problems

In a first aspect of the present invention, there is provided a multi-micro hollow cathode light source, which emits light through generation of micro hollow plasma in an atmosphere gas, characterized in that the light source comprises: a cathode plate formed of a metal having high secondary electron emission coefficient; an insulation plate; an anode plate disposed by the mediation of an insulation plate to the cathode plate; a single hole penetrating the cathode plate, the insulation plate, and the anode plate and having a diameter of 1 cm or less; a plurality of metal pieces containing elements which provide a plurality of bright line spectra attributed to the elements; and an atmosphere gas, wherein the cathode plate has a plurality of slots radially and continuously extending from the hole, and the plurality of metal pieces are received by the slots.

The amount of each metal piece may be modified in accordance with the material of the piece. Also, the amount of each metal piece may be readily modified in accordance with the thickness of each piece, the number of the pieces received by one slot, etc. The thickness and the piece number may be readily adjusted by modifying the width of a corresponding slot. Each slot may receive a plurality of metal pieces, and the metal pieces may be formed of the same material or materials different from one another. Some of the slots may receive a metal piece formed of the same material. Through tuning the amount of each metal piece, the spectral intensity of a metal element of interest may be controlled.

No particular limitation is imposed on the configuration pattern of the slots, so long as the slots radially extend from the hole. In one exemplary configuration, four slots extend from the hole in a cross shape. Preferably, the slots penetrate the cathode plate in an orthogonal direction to the main surface thereof. In this case, the length of the metal piece received by a slot along the axial direction of the hole increases, and the area of a portion of the piece exposed to the inner wall of the hole increases, whereby the sputtering efficiency of the metal piece increases, leading to an increase in spectral intensity of a metal element. From another aspect, penetration of a metal piece through a slot is advantageous in ease of production. Provision of an excessive number of the slots and an excessive width of each slot are not preferred, since the area of the metal having high secondary electron emission coefficient which is exposed to the inner wall of the hole decreases, causing a drop in metal piece sputtering efficiency. Therefore, the number of slots is preferably about 2 to about 8, and the width of each slot is preferably about 0.1 to about 0.9 times the diameter of the hole.

The hole preferably has a diameter of 1 mm or less, since plasma can be confined in the hole at high density. Such a diameter is advantageous for providing a single-point light source. The light source of the present invention is designed to be employed with an atmosphere gas at an atmospheric pressure or slightly lower. Upon attainment of a broad emission (e.g., excimer), the light source may also be employed under pressurized conditions. Generally, as the atmosphere gas pressure increases, the diameter of the hole can be reduced. In consideration of the above pressure at which the light source is used, the diameter of the hole is preferably 10 µm or more. The diameter of the hole in the insulation plate is preferably slightly larger than that of the diameter of the hole in the cathode plate or in the anode plate. Specifically, the diameter of the hole in the insulation plate is preferably larger by 100 µm to 1,000 µm than that of the diameter of the hole in the cathode plate or in the anode plate, in order to prevent melting of the insulation plate during electric discharge.

The atmosphere gas employed in the invention is preferably an inert gas such as He, Ne, Ar, Kr, or Xe, with He and Ne being particularly preferred, since high efficiency of secondary electron emission from metal can be attained.

Examples of the material of the cathode plate; i.e., the metal having secondary electron emission coefficient, include at least one of copper, copper alloy, silver, silver alloy, molybdenum, molybdenum alloy, tungsten, and tungsten alloy. The metal preferably has a secondary electron emission coefficient of 0.2 or higher, more preferably 1.0 or higher. Among them, copper or copper alloy is preferred, from the viewpoints of low cost (high availability) and high secondary electron emission coefficient and thermal conductivity. Also, the anode plate is preferably formed of copper or copper alloy.

A second aspect of the invention is directed to a specific embodiment of the multi-micro hollow cathode light source of the first aspect, wherein the metal having high secondary electron emission coefficient is copper or a copper alloy.

A third aspect of the invention is directed to a specific embodiment of the multi-micro hollow cathode light source of the first or second aspect, wherein the atmosphere gas is helium.

A fourth aspect of the invention is directed to a specific embodiment of the multi-micro hollow cathode light source of the first to third aspects, wherein the hole has a diameter of 1 mm or less.

In a fifth aspect of the present invention, there is provided an atomic absorption spectrometer for simultaneously determining a plurality of elements, characterized by comprising a multi-micro hollow cathode light source as recited in the first to fourth aspects of the invention.

Effects of the Invention

According to the present invention, a plurality of metal pieces exposed to the inner wall of the hole provided in the cathode plate can be simultaneously sputtered at high efficiency, whereby a high-density plasma of a plurality of metal elements can be formed. As a result, bright line spectra corresponding to a plurality of metal elements of interest can be obtained. The light source of the present invention, having only a single hole, serves as a single-point light source. Thus, an optical path configuration for utilization of light can be easily established. For example, by use of the light source of the present invention, an apparatus such as an atomic absorption spectrometer can be produced at low cost. Since discharge occurs at one single hole, electric discharge can be readily controlled. The intensity of the bright line spectrum can be readily controlled by modifying the number of metal pieces received in the slots or other conditions.

MODES FOR CARRYING OUT THE INVENTION

Hereinafter, embodiments of the present invention will be described with reference to the drawings. The embodiments should not be construed as limiting the present invention thereto.

Embodiment 1

Figure 1:
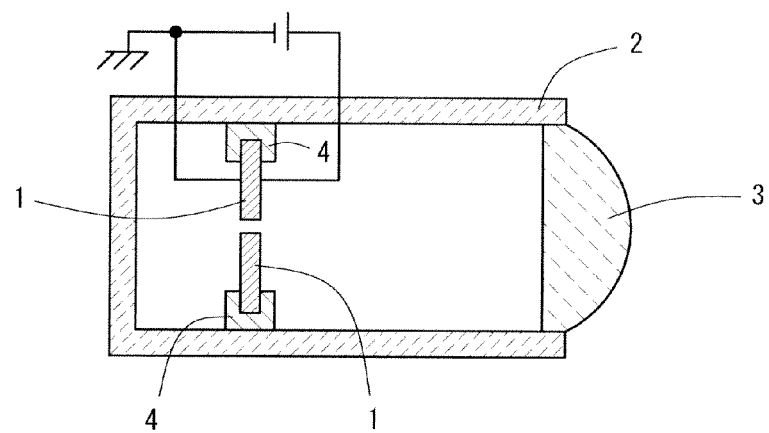
FIG. 1 A schematic view of the configuration of the multi-micro hollow cathode light source of Embodiment 1.

FIG. 1 is a schematic view of the configuration of the multi-micro hollow cathode light source of Embodiment 1. The multi-micro hollow cathode light source has an electrode plate 1, a casing 2, a lens 3, and an electrode plate-fixing member 4. The casing 2, which is made of glass, provides a sealed, hollow cylindrical space. The electrode plate-fixing member 4 is disposed in the inside of the casing 2. In the casing 2, the electrode plate-fixing member 4 is adapted to affix the electrode plate 1 so that the plate face aligns the axial direction of the cylinder. The casing 2 is filled with helium gas. The casing 2 has, on one side along the axial direction of the cylinder, a lens 3 for condensing light beams emitted in the casing 2 and for outputting the condensed light.

The casing 2 may be provided with piping, so that helium gas in the casing 2 can be circulated, and the internal pressure can be regulated. For enhancing the emission intensity, the internal pressure is preferably adjusted to 0.01 to 0.1 atm.

Figure 2:
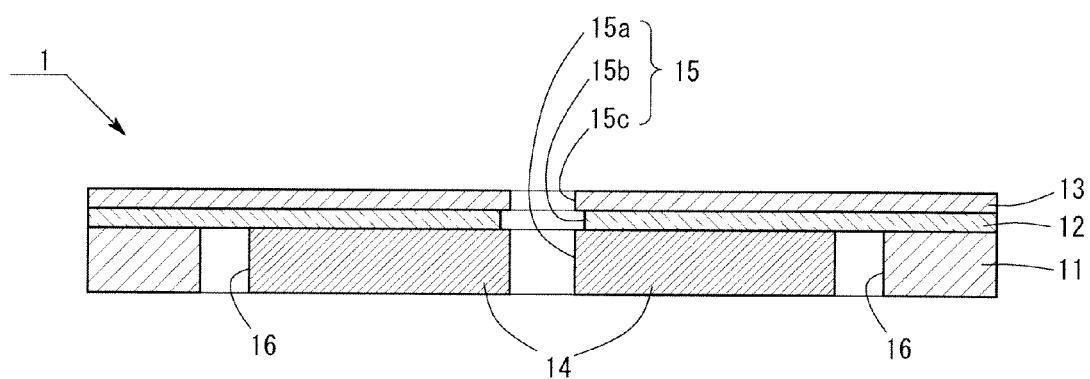
FIG. 2 A cross-section of the electrode plate 1.

FIG. 2 is an enlarged cross-section of the structure of the electrode plate 1. As shown in FIG. 2, the electrode plate 1 is formed of a cathode plate 11, an insulation plate 12, an anode plate 13, and metal pieces 14. The insulation plate 12 is sandwiched between the cathode plate 11 and the anode plate 13. The cathode plate 11 and anode plate 13 are formed of copper, and the insulation plate 12 is formed of a ceramic material. The cathode plate 11 and anode plate 13 are electrically connected via wiring to a power source, respectively. By means of the power source, the cathode plate 11 is grounded, and a positive voltage is applied to the anode plate 13. Needless to say, the anode plate 13 may be grounded, and a negative voltage may be applied to the cathode plate 11.

The cathode plate 11 has a thickness of 1 mm, and the insulation plate 12 and anode plate 13 each have a thickness of 0.3 mm. The cathode plate 11, insulation plate 12, and anode plate 13 are in the circular shape having a diameter of 2 cm. The centers of the cathode plate 11, the insulation plate 12, and the anode plate 13 are provided with holes 15a, 15b, and 15c, respectively. The holes 15a to 15c are concentrically disposed, to provide a penetrating through-hole 15. The hole 15a in the cathode plate 11 and the hole 15c in the anode plate 13 each have a diameter of 1 mm, and the hole 15b in the insulation plate 12 has a diameter of 1.2 mm. The diameter of the hole 15b in the insulation plate 12 is adjusted to be slightly greater than that of the hole 15a in the cathode plate 11 and that of the hole 15c in the anode plate 13, so as to prevent the insulation plate 12 from melting during electric discharge.

Figure 3:
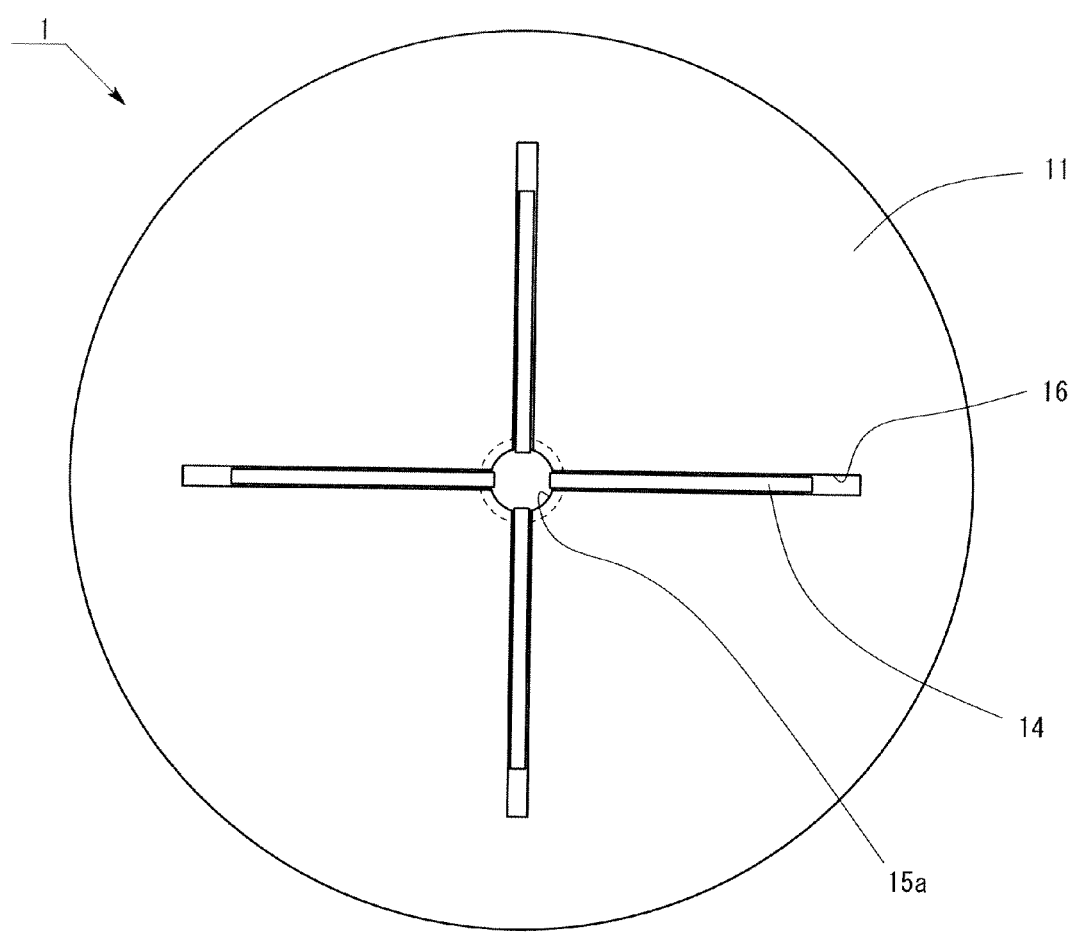
FIG. 3 A plan view of the electrode plate 1 as viewed from the cathode plate 11.

FIG. 3 is a plan view of the electrode plate 1 as viewed from the cathode plate 11. As shown in FIG. 3, the cathode plate 11 is provided with four linear slots 16 radially and continuously extending from the hole 15a in a cross shape. These slots 16 penetrate the cathode plate 11. Each slot 16 has a width of 0.2 mm and a length of 6 mm. Four metal pieces 14 made of materials different from one another are inserted and buried in the four slots 16. The four metal pieces 14 are formed of Zn, Cd, Pb, and Cr, respectively. Each metal piece 14 assumes a rectangular shape (1 mm×5 mm) having a thickness of 0.2 mm.

Next, the principle of light emission of the multi-micro hollow cathode light source of Embodiment 1 will be described.

When voltage is applied between the cathode plate 11 and the anode plate 13, helium gas contained in the casing 2 is ionized, to thereby generate a plasma in the hole 15 and in the vicinity of the opening. Ions in the plasma are drawn through the electric field to the cathode plate 11 and caused to collide therewith. Through the ion impact, Cu ions and electrons forming the cathode plate 11 are dissociated. The thus-released electrons, which are called secondary electrons, promote further ionization of atoms, leading to effective plasma generation.

Since the cathode plate 11 is formed of copper, having high secondary electron emission coefficient, a plasma can be generated in the hole 15 and in the vicinity of the opening. The high-density plasma generated in the hole 15 effectively sputters four metal pieces 14 exposed to the inner wall of the hole 15a. As a result, a plasma of five elements: Zn, Cd, Pb, Cr (metal elements forming the metal pieces 14), and Cu (the material of the cathode plate 11) can be generated at high density. Thus, the emission spectrum of the micro hollow cathode discharge includes bright lines attributed to five metal elements of Zn, Cd, Pb, Cr, and Cu.

As described above, the multi-micro hollow cathode light source of Embodiment 1 can provide light including bright line spectra attributed to a plurality of metal elements, although the light source is a single-point light source based on micro hollow cathode discharge.

Figure 4:
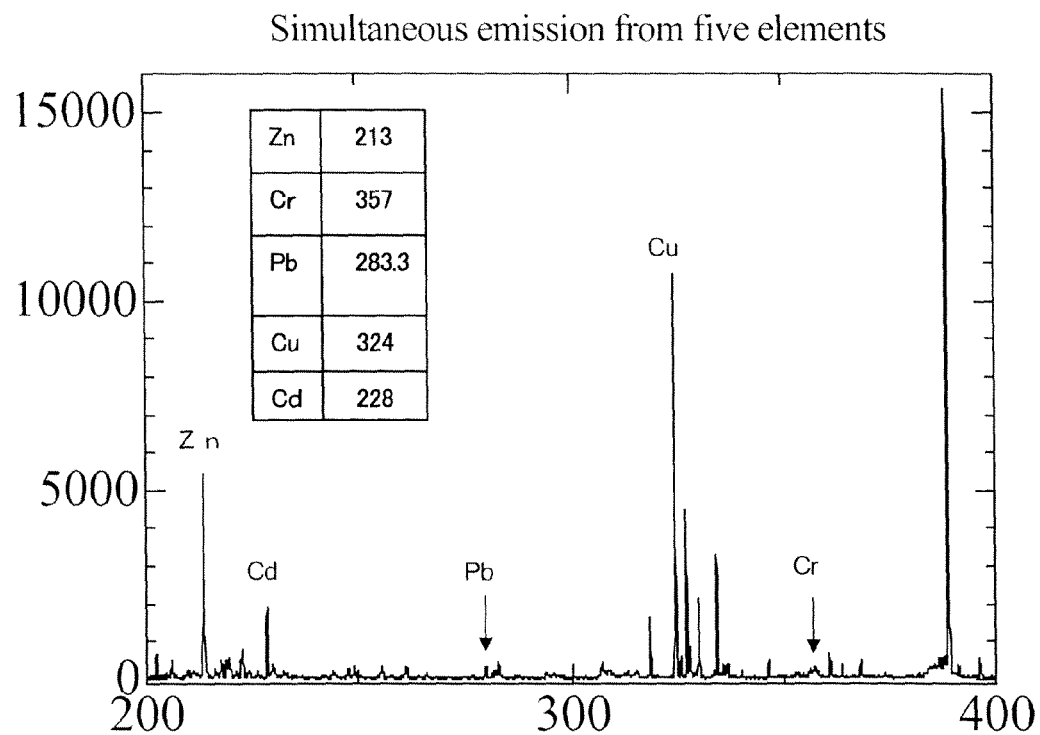
FIG. 4 An emission spectrum.

FIG. 4 is an emission spectrum. In measurement, the current and internal pressure were adjusted to 25 mA and 0.05 atm, respectively. As is clear from the spectrum, bright lines attributed to Zn, Cr, Pb, Cu, and Cd were assigned to wavelengths of 213 nm, 357 nm, 283.3 nm, 324 nm, and 228 nm, respectively. That is, light including bright lines attributed to five metal elements was found to be obtained from the multi-micro hollow cathode light source. As shown in the spectrum, the intensities of emission attributed to Pb and Cr were low, and the bright lines were relatively broad as compared with those of Zn, Cu, and Cd. However, if the width of each slot 16 is increased, and the number of metal pieces 14 made of Pb and Cr is increased, or the thickness of each metal piece 14 is increased, the intensities of emission attributed to Pb and Cr can be enhanced, whereby more clear bright lines can be obtained.

Embodiment 2

Figure 5:
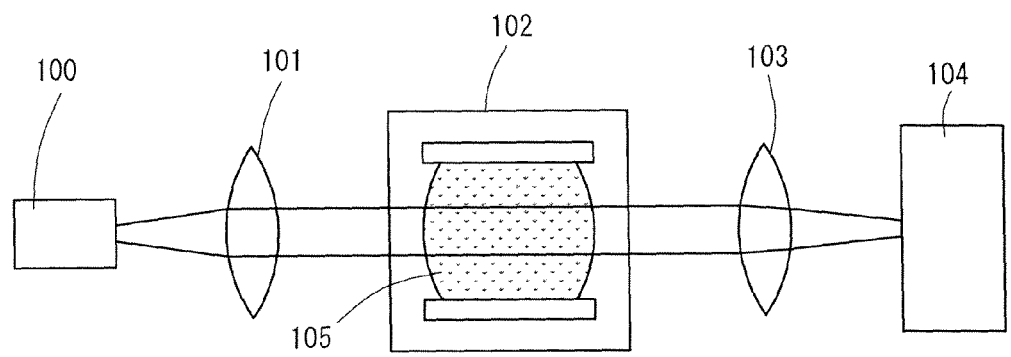
FIG. 5 A schematic view of the structure of the atomic absorption spectrometer of Embodiment 2.

Embodiment 2 is an atomic absorption spectrometer employing the multi-micro hollow cathode light source of Embodiment 1. As shown in FIG. 5, the atomic absorption spectrometer has a multi-micro hollow cathode light source 100 (Embodiment 1), a collimator lens 101, a sputtering apparatus 102, a condensing lens 103, and a light-receiving element array 104. The multi-micro hollow cathode light source 100 emits light including bright lines attributed to a plurality of metal elements, which are targets of measurement. The sputtering apparatus 102 forms a plasma of a sample. The light including bright lines attributed to a plurality of metal elements emitted by the multi-micro hollow cathode light source 100 is transformed into parallel light beams by means of the collimator lens 101, and a plasma 105 in the sputtering apparatus 102 is irradiated with the parallel light beams. The parallel light beams which have passed through the plasma 105 are condensed by means of the condensing lens 103, and the condensed light reaches the light-receiving element array 104. As a result, a plurality of metal elements (measurement targets) in the plasma 105 can be identified. Through measurement of percent atomic absorption of each element, the densities of the metal elements can be simultaneously determined.

Since the atomic absorption spectrometer employs the multi-micro hollow cathode light source 100 of Embodiment 1 as a light source, only one optical axis is provided. Thus, an optical path from the light source to the light-receiving element array 104 can be constructed in a very simple manner. Therefore, the atomic absorption spectrometer can be produced on a small scale and at low cost.

In Embodiment 2, a sample was atomized at high temperature through sputtering to generate a plasma. Alternatively, atomization techniques conventionally employed in atomic absorption spectrometry such as laser ablation, flame, and electric heating may also be employed.

INDUSTRIAL APPLICABILITY

The multi-micro hollow cathode light source of the present invention may be employed in atomic absorption spectrometry and the like.

DESCRIPTION OF REFERENCE NUMERALS

1: Electrode plate
2: Casing
3: Lens
4: Electrode plate-fixing member
11: Cathode plate
12: Insulation plate
13: Anode plate
14: Metal piece
15: Hole
16: Slot
100: Multi-micro hollow cathode light source
101: Collimator lens
102: Sputtering apparatus
103: Condensing lens
104: Light-receiving element array

The invention claimed is:

1. A multi-micro hollow cathode light source, which emits light through generation of micro hollow plasma in an atmosphere gas, the light source comprising:
a cathode plate formed of a metal having high secondary electron emission coefficient;
an insulation plate;
an anode plate disposed by the mediation of an insulation plate to the cathode plate;
a single hole penetrating the cathode plate, the insulation plate, and the anode plate; and
a casing holding the cathode plate, the insulation plate, and the anode plate;
wherein the cathode plate has a plurality of slots radially and continuously extending from the hole, and the slots are provided to receive a plurality of metal pieces containing elements which provide a plurality of bright line spectra attributed to the elements.

2. The multi-micro hollow cathode light source according to claim 1,
wherein the hole comprises a diameter of 1 cm or less.

3. The multi-micro hollow cathode light source according to claim 2, further comprising:
a plurality of metal pieces containing elements which provide a plurality of bright line spectra attributed to the elements.

4. The multi-micro hollow cathode light source according to claim 2, further comprising:
an atmosphere gas in the casing.

5. The multi-micro hollow cathode light source according to claim 2, wherein the metal having high secondary electron emission coefficient is copper or a copper alloy.

6. The atomic absorption spectrometer for simultaneously assaying a plurality of elements, the spectrometer comprising a multi-micro hollow cathode light source according to claim 2.

7. The multi-micro hollow cathode light source according to claim 1, comprising:

a plurality of metal pieces containing elements which provide a plurality of bright line spectra attributed to the elements.

8. The multi-micro hollow cathode light source according to claim 7, further comprising:
an atmosphere gas in the casing.

9. The multi-micro hollow cathode light source according to claim 7, wherein the metal having high secondary electron emission coefficient comprises copper or a copper alloy.

10. The multi-micro hollow cathode light source according to claim 7, wherein the hole comprises a diameter of 1 mm or less.

11. The atomic absorption spectrometer for simultaneously assaying a plurality of elements, the spectrometer comprising a multi-micro hollow cathode light source according to claim 7.

12. The multi-micro hollow cathode light source according to claim 1, further comprising:
an atmosphere gas in the casing.

13. The multi-micro hollow cathode light source according to claim 12, wherein the atmosphere gas comprises helium.

14. The multi-micro hollow cathode light source according to claim 13, wherein the hole comprises a diameter of 1 mm or less.

15. The multi-micro hollow cathode light source according to claim 1, wherein the metal having high secondary electron emission coefficient is copper or a copper alloy.

16. The multi-micro hollow cathode light source according to claim 15, wherein the hole comprises a diameter of 1 mm or less.

17. The atomic absorption spectrometer for simultaneously assaying a plurality of elements, the spectrometer comprising a multi-micro hollow cathode light source according to claim 15.

18. The multi-micro hollow cathode light source according to claim 1, wherein the hole comprises a diameter of 1 mm or less.

19. The atomic absorption spectrometer for simultaneously assaying a plurality of elements, the spectrometer comprising a multi-micro hollow cathode light source according to claim 18.

20. The atomic absorption spectrometer for simultaneously assaying a plurality of elements, the spectrometer comprising a multi-micro hollow cathode light source according to claim 1.

* * * * *